US011793939B2

(12) United States Patent
Cowe et al.

(10) Patent No.: US 11,793,939 B2
(45) Date of Patent: Oct. 24, 2023

(54) MEDICAMENT DELIVERY DEVICES

(71) Applicant: Owen Mumford Limited, Woodstock (GB)

(72) Inventors: Toby Cowe, Woodstock (GB); Timothy Evans, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 263 days.

(21) Appl. No.: 16/968,002

(22) PCT Filed: Feb. 6, 2019

(86) PCT No.: PCT/GB2019/050318
§ 371 (c)(1),
(2) Date: Aug. 6, 2020

(87) PCT Pub. No.: WO2019/155203
PCT Pub. Date: Aug. 15, 2019

(65) Prior Publication Data
US 2021/0244885 A1    Aug. 12, 2021

(30) Foreign Application Priority Data
Feb. 6, 2018   (GB) ..................... 1801896

(51) Int. Cl.
*A61M 5/24* (2006.01)
*A61M 5/32* (2006.01)
(Continued)

(52) U.S. Cl.
CPC .......... *A61M 5/2466* (2013.01); *A61M 5/288* (2013.01); *A61M 5/3202* (2013.01); *A61M 5/345* (2013.01); *A61M 2005/2474* (2013.01)

(58) Field of Classification Search
CPC .............. A61M 5/3202; A61M 5/2466; A61M 5/2033; A61M 5/2422; A61M 5/2429;
(Continued)

(56) References Cited

U.S. PATENT DOCUMENTS 3,401,693 A   9/1968 Cohen
6,902,543 B1  6/2005 Cherif-Cheikh et al.
(Continued)

FOREIGN PATENT DOCUMENTS

CN   103347556 A   10/2013
CN   107530506 A    1/2018
(Continued)

OTHER PUBLICATIONS

International Search Report and Written Opinion of the International Searching Authority from corresponding PCT Application No. PCT/GB2019/050318, dated May 21, 2019 (13 pages).
(Continued)

*Primary Examiner* — Jenna Zhang
(74) *Attorney, Agent, or Firm* — Quarles & Brady LLP

(57) ABSTRACT

A medicament delivery device is disclosed, comprising a cartridge assembly that comprises a cartridge having a medicament chamber for containing a medicament, a sealing element for sealing a distal end of the medicament chamber and a coupling element attached to the cartridge. The device also includes a sealing element release member, a cannula for delivery of the medicament, and a removable cap. The device is switchable from a starting configuration in which the release member is spaced from the sealing element to an activated configuration in which the release member cooperates with the sealing element to connect the medicament chamber to the cannula. A proximal end of the release
(Continued)

member is sealed in a release member chamber defined in part by, the sealing element and in part by the coupling element.

15 Claims, 8 Drawing Sheets

(51) Int. Cl.
  *A61M 5/28* (2006.01)
  *A61M 5/34* (2006.01)
(58) Field of Classification Search
  CPC ........ A61M 5/2455; A61M 2005/2407; A61M 2005/247; A61M 2005/2006; A61M 2005/2026; A61M 2005/2073; A61M 2005/208; A61M 2005/2474
  See application file for complete search history.

(56) References Cited

U.S. PATENT DOCUMENTS

| | | | |
|---|---|---|---|
| 9,867,944 B1 | 1/2018 | Justus | |
| 10,518,023 B2 * | 12/2019 | Archilla | A61M 5/2466 |
| 11,273,264 B2 * | 3/2022 | Okihara | A61M 5/5086 |
| 2005/0075602 A1 | 4/2005 | Cherif-Cheikh et al. | |
| 2009/0171311 A1 | 7/2009 | Genosar et al. | |
| 2013/0331796 A1 * | 12/2013 | Wozencroft | A61M 5/3204 604/197 |
| 2016/0346483 A1 | 12/2016 | Fourt et al. | |
| 2018/0353704 A1 * | 12/2018 | Helmer | A61M 5/2033 |
| 2018/0369497 A1 * | 12/2018 | Schader | A61M 5/3204 |

FOREIGN PATENT DOCUMENTS

| | | | | |
|---|---|---|---|---|
| EP | 0239673 A2 | 10/1987 | | |
| EP | 0602883 A2 | 6/1994 | | |
| WO | 2008067467 A2 | 6/2008 | | |
| WO | 2017009640 A1 | 1/2017 | | |
| WO | WO-2017009640 A1 * | 1/2017 | ............... | A61J 1/06 |
| WO | 2017089270 A1 | 6/2017 | | |

OTHER PUBLICATIONS

Search Report, related UK Application No. GB 1801896.0, dated Jul. 11, 2018, 2 pages.
China National Intellectual Property Administration, Second Office Action from corresponding CN Application No. 201980011868.2, dated Oct. 8, 2022 (11 pages).

\* cited by examiner

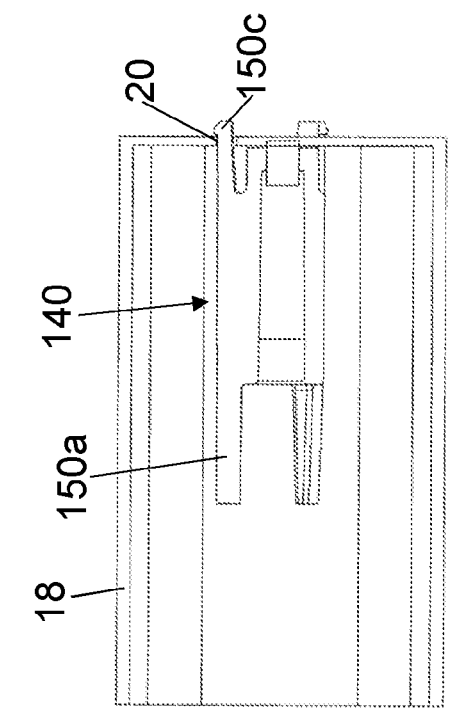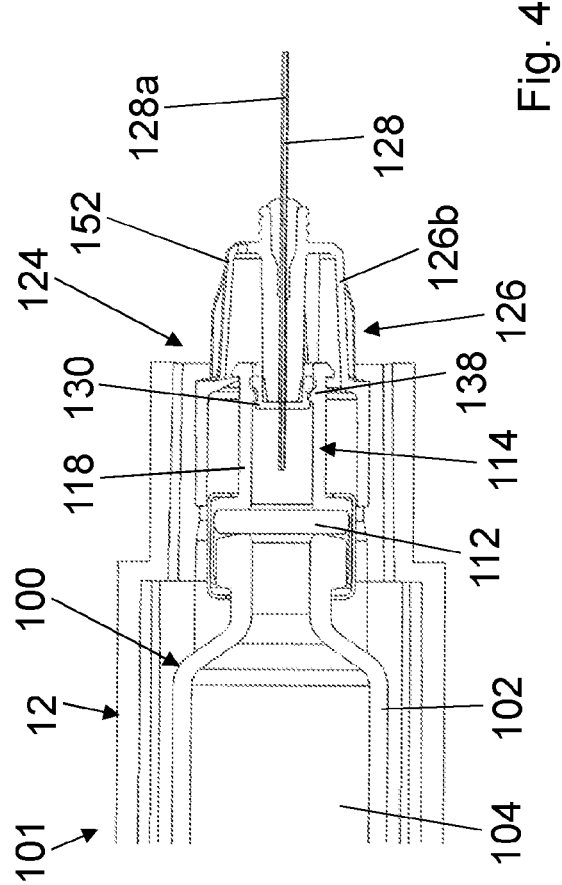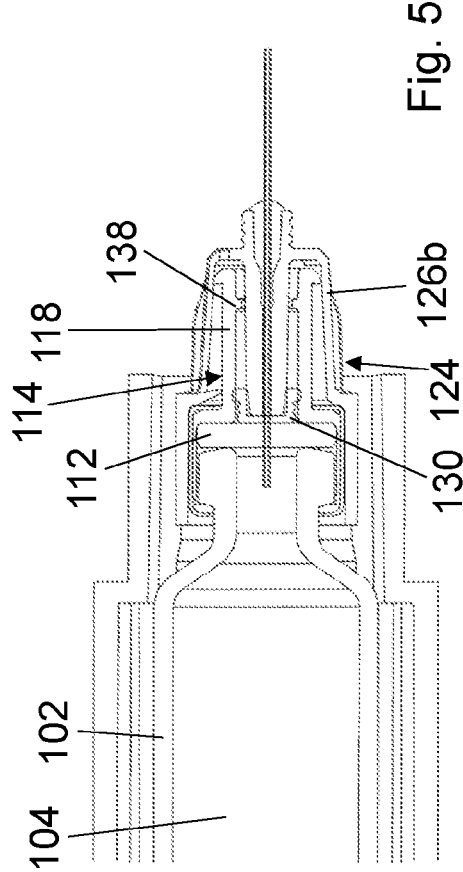
Fig. 4
Fig. 5

MEDICAMENT DELIVERY DEVICES

CROSS-REFERENCE TO RELATED APPLICATIONS

This application represents the U.S. National Stage of International Application No. PCT/GB2019/050318 filed Feb. 6, 2019, which claims priority to British Patent Application Serial No. GB 1801896.0, filed Feb. 6, 2018, and entitled, "MEDICAMENT DELIVERY DEVICES", all of which are incorporated herein by reference in their entirety.

FIELD OF THE INVENTION

The present invention relates to medicament delivery devices. In particular, but not exclusively, the invention relates to medicament delivery devices in which the medicament is stored in a pre-filled cartridge within the device.

BACKGROUND TO THE INVENTION

The present applicant's International Patent Application Publication No. WO 2017/009640 A1, the contents of which are hereby incorporated by reference, describes medicament delivery devices in which the medicament is contained within a cartridge that is sealed with a sealing element in the form of a septum. The cartridges are arranged to engage with devices that include a release member that is arranged to pierce the septum when the cartridge is inserted into the device.

Compared with a pre-filled syringe having a staked needle, the medicament packaging arrangements described in WO 2017/009640 A1 allow greater choice in the type of cannula used to deliver the medicament and a higher degree of design freedom in the delivery devices, whilst maintaining the advantages of a simple, universal primary package.

In some embodiments disclosed in WO 2017/009640 A1, the cartridge is arranged to engage with the device in two positions. In a first engagement position, the release member is spaced from the septum so that the medicament remains sealed in the cartridge. The device can be sold, transported and handled in this state. To prepare the device for delivery of the medicament, the cartridge is moved into a second engagement position relative to the device, in which the release member pierces the septum to allow the medicament to flow to the cannula.

The present invention provides further improvements to medicament packaging and medicament delivery devices.

SUMMARY OF THE INVENTION

In a first aspect of the present invention, there is provided a medicament delivery device comprising a cartridge assembly that comprises a cartridge having a medicament chamber for containing a medicament, a sealing element for sealing a distal end of the medicament chamber, and a coupling element attached to the cartridge. The device also includes a sealing element release member, a cannula for delivery of the medicament, and a removable cap. The device is switchable by relative movement between the release member and the cartridge assembly from a starting configuration in which the release member is spaced from the sealing element to an activated configuration in which the release member cooperates with the sealing element to connect the medicament chamber to the cannula. A release member chamber is defined in part by the coupling element and in part by the sealing element. The release member chamber is arranged for receiving the release member such that at least a proximal end of the release member is sealed in the release member chamber when the device is in the starting configuration. The cap comprises at least one blocking formation that cooperates with the coupling element for limiting relative movement between the release member and the cartridge assembly in at least one direction, thereby to keep the device in the starting configuration when the cap is in place.

With this arrangement, the risk of unintentional activation of the device is decreased. In particular, by providing the blocking formation, the cartridge assembly is prevented from moving distally towards the release member if the device were to be dropped onto its distal end, or due to mishandling creating similar loads. Furthermore, because the blocking formation cooperates with the coupling element of the cartridge assembly, the blocking formation does not intrude into the release member chamber nor otherwise interfere with the sealing of the proximal end of the release member in the release member chamber. In this way, the proximal end of the release member can remain sterile in the release member chamber until the device is prepared for use.

The cap may be disposed at a distal end of the device. A proximal end of the or each blocking formation may cooperate with the coupling element to limit relative movement between the release member and the cartridge assembly. For example, a proximal tip of the or each blocking formation may abut the coupling element. The or each blocking formation may for example comprise a proximally extending finger or a radially inwardly projecting rib of the cap. Preferably, removal of the cap causes the or each blocking formation to move linearly to separate from the coupling element.

The release member may be fixed in position with respect to the cap when the cap is in place. For example, the release member may be mounted in a hub, and the cap may be engageable with the hub. The cannula may be mounted in the hub.

The hub may be moveable with respect to a housing of the device and the cartridge assembly to switch the device from the starting configuration to the activated configuration. Alternatively, the hub may be fixed with respect to a housing of the device and the cartridge assembly may be moveable with respect to the hub to switch the device from the starting configuration to the activated configuration.

The or each blocking formation may extend through a corresponding aperture in the hub to cooperate with the coupling element of the cartridge assembly.

When a hub is provided, the release member chamber is preferably defined in part by the hub. Preferably, an aseptic seal is formed between the hub and the coupling element to seal the release member chamber at least when the assembly is in the starting configuration. The device may comprise a seal member arranged to provide the aseptic seal between the hub and the coupling element. The seal member may be elastomeric.

The hub may comprise a proximally-projecting boss for the release member and the release member chamber may be defined in part by a distally-projecting tubular member of the coupling element. The tubular member may be arranged to receive the boss and the aseptic seal may be formed between the tubular member and the boss at least when the assembly is in the starting configuration. When the aseptic seal is provided by a seal member, the seal member may for example comprise an O-ring disposed between the tubular member and the boss or a cap disposed over a proximal end of the boss.

The device may include a cannula chamber defined in part by the cap and arranged for receiving the cannula such that at least a distal end of the cannula is sealed in the cannula chamber when the cap is in place.

The cap may include a vent for venting the cannula chamber. The vent may comprise an air permeable sterile barrier material. In this way, the pressures within the cannula chamber and the release member chamber, when provided, are equalised with the pressure outside the device, eliminating a pressure gradient across the seals that close the respective chambers and therefore reducing the risk of seal failure.

In one arrangement, the cap comprises a cap sleeve member and an outer cap and the cannula chamber is defined in part by the cap sleeve member. The outer cap may be engageable with a housing of the device and the cap sleeve member may be engageable with the outer cap during assembly of the device. The cap sleeve member may instead be integrally formed with the outer cap.

The release member may comprise a tubular element arranged to pierce the sealing element upon switching of the assembly into the activated configuration. Preferably, the cannula comprises a distal part of a needle and the release member comprises a proximal part of the needle.

In another aspect of the invention, a medicament delivery device includes a cartridge assembly comprising a cartridge having a medicament chamber for containing a medicament and a sealing element for sealing a distal end of the medicament chamber. The device also includes a sealing element release member, a cannula for delivery of the medicament, and a removable cap. The device is switchable by relative movement between the release member and the cartridge assembly from a starting configuration in which the release member is spaced from the sealing element to an activated configuration in which the release member cooperates with the sealing element to connect the medicament chamber to the cannula. The cap comprises at least one blocking formation that cooperates with the cartridge assembly for limiting relative movement between the release member and the cartridge assembly in at least one direction, thereby to keep the device in the starting configuration when the cap is in place.

Preferred and/or optional features of each aspect of the invention may be used, alone or in appropriate combination, in the other aspects also.

BRIEF DESCRIPTION OF THE DRAWINGS

Embodiments of the present invention will now be described, by way of example only, with reference to the accompanying drawings, in which like reference numerals are used for like features, and in which:

FIG. 4 is a cross-sectional view of part of the delivery device of FIG. 1 after removal of a cap;

FIG. 5 is a cross-sectional view of part of the delivery device of FIG. 1 when switched to an activated configuration;

Figure 1:
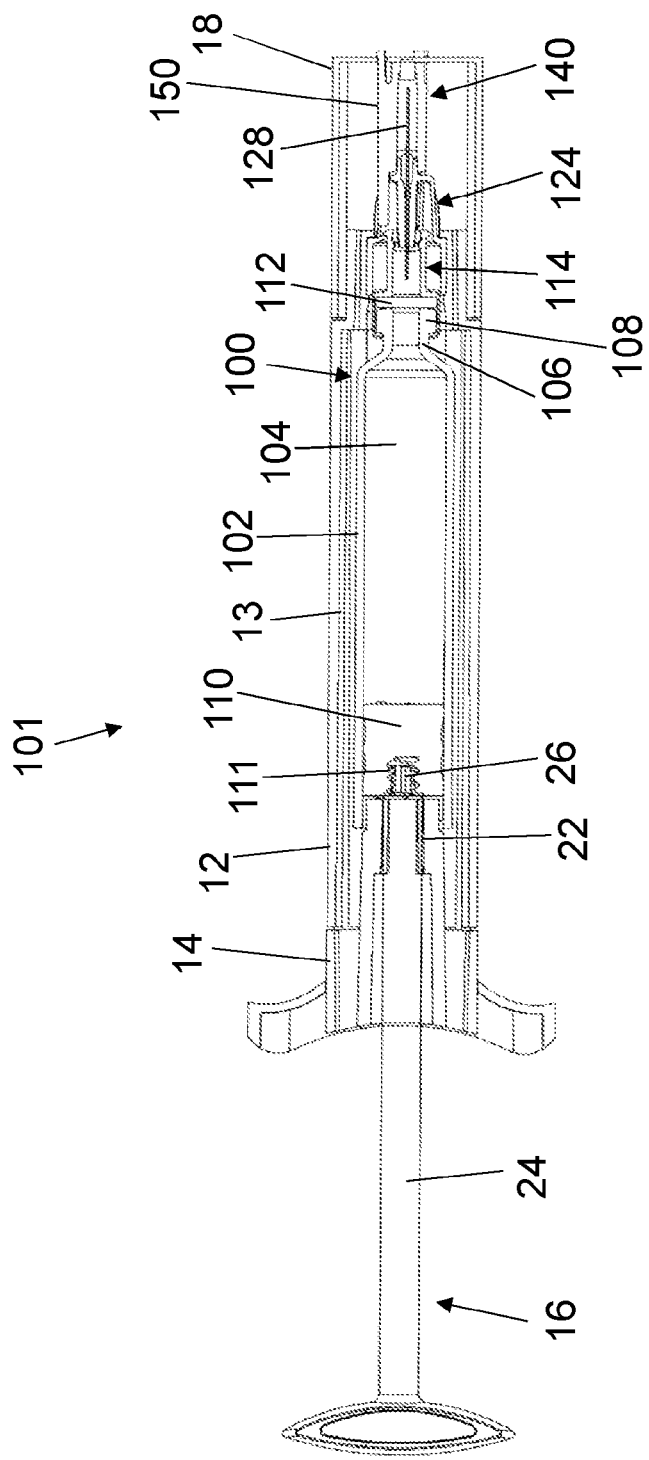
FIG. 1 is a cross-sectional view of a medicament delivery device according to the invention when in a starting configuration.
Figure 2:
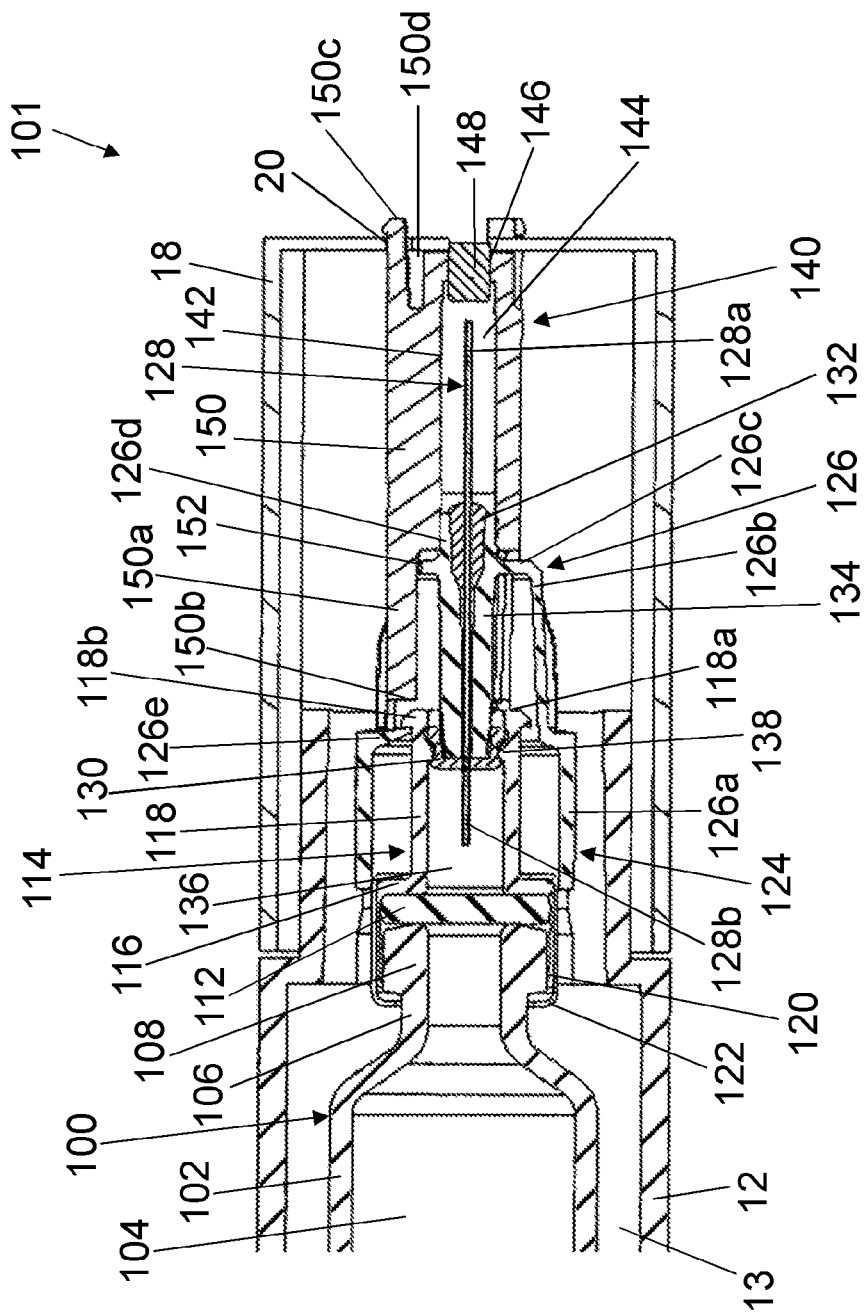
FIG. 2 is a cross-sectional view of part of the device of FIG. 1 on an enlarged scale.

Throughout this specification, the term "distal" and related terms are used to refer to the end of the device that is closest to the injection site in use (i.e. to the right in FIGS. 1 and 2), and the term "proximal" and related terms are used to refer to the opposite end of the device (i.e. to the left in FIGS. 1 and 2).

DESCRIPTION OF THE PREFERRED EMBODIMENTS

FIGS. 1 and 2 show a medicament delivery device 101 according to a first embodiment of the invention.

As shown in FIG. 1, the device 101 comprises a device housing 12, a proximal end fitting 14 and a plunger 16. An outer cap 18 is provided at the distal end of the housing. The outer cap 18 engages with the housing 12 and is removable in use of the device 101. In this example, the device 101 comprises a manually-operated syringe.

The housing 12 of the device 101 defines an interior space 13 that accommodates a cartridge assembly 100. The cartridge assembly comprises a cartridge 102 having a medicament chamber 104 for containing a medicament. The cartridge 102 is generally tubular and has a reduced-diameter neck 106 at its distal end. As can be seen most clearly in FIG. 2, an annular collar 108 extends around the neck 106. A piston member comprising a stopper or bung 110 (see FIG. 1) is inserted into the proximal end of cartridge 102 to close the proximal end of the medicament chamber 104.

Referring particularly to FIG. 2, the distal end of the cartridge 102 is closed by a sealing element in the form of a disc-shaped elastomeric septum 112. The septum 112 is clamped against the distal end face of the cartridge 102 by a coupling element 114. The coupling element 114 includes a ring-shaped annular clamping portion 116 that bears against the septum 112, leaving a central part of the septum 112 uncovered by the coupling element 114. A tubular throat 118 extends distally from the clamping portion 116 to provide an engagement portion of the coupling element 114. The throat 118 has a smaller diameter than the clamping portion 116. In this embodiment, a tubular skirt 120 extends proximally from the clamping portion 116, with the collar 108 of the cartridge 102 and the septum 112 being received in the skirt 120. The skirt 120 helps to centre the septum 112 and the coupling element 114 with respect to the cartridge 102 during assembly. In other embodiments the skirt 120 may be omitted.

In this example, the coupling element 114 is attached to the cartridge 102 by a crimp fitting, which in this embodiment comprises a crimp ring 122, preferably formed of a ductile metal such as aluminium. During assembly, the tubular crimp ring 122 is mounted over the skirt 120 and the clamping portion 116 of the coupling element 114 and the ends of the ring 122 are bent inwardly around the proximal side of the collar 108 and the distal side of the clamping portion 116. With the crimp ring 122 in place, the clamping portion 116 of the coupling element 114 applies a clamping force to the septum 112 to seal the septum 112 against the distal end of the cartridge 102.

The coupling element 114 cooperates with a hub subassembly 124. The hub subassembly 124 comprises a hub body 126, a cannula in the form of a double-ended hypodermic needle 128, a seal member comprising an elastomeric sealing cap 130 for forming a seal between the hub body 126 and the coupling element 114, and a cannula seal 132 for forming a seal between the hub body 126 and the needle 128.

The hub body 126 comprises a generally tubular proximal part 126a and a bell-shaped distal part 126b. The distal end of the hub body 126 has an end face 126c with a central aperture for receiving the needle 128. A tubular cap retaining part 126d surrounds the aperture and extends distally from the end face 126c. The needle 128 is fixed in the aperture by the cannula seal 132, which may for example be of a suitable elastomeric material. A distal end part 128a of the needle 128 projects away from the hub body 126.

A generally tubular boss 134 extends proximally from the end face 126c of the hub body 126, towards the proximal part 126a. The sealing cap 130 fits over the proximal end of the boss 134, and a proximal end part 128b of the needle 128 extends through the cap 130 to project into a release member chamber 136 defined by the septum 112, the tubular throat 118 of the coupling element 114 and the elastomeric cap 130 of the hub subassembly 124. The sealing cap 130 provides a seal member that forms a seal against the inner wall of the throat 118 of the coupling element 114, and is shaped to locate with an inward projection in the form of an annular ridge 138 formed on the inner wall of the throat 118.

The chamber 136 provides an aseptically sealed compartment for the proximal end part 128b of the needle 128. Thus, provided the cartridge assembly 100 and the hub subassembly 124 are assembled in sterile conditions, the proximal end part 128b of the needle 128 remains sterile until the device 101 is activated, as will be described below.

Distal movement of the hub subassembly 124 away from the coupling element 114 is prevented by a clip formation. As can be seen most clearly in FIG. 2, the clip formation is formed by a plurality of flexible clips or barbs 126e that extend inwardly from the distal end of the proximal part 126a of the hub body 126 to engage with a collar 118b formed at the distal end of the throat 118 of the coupling element 114. The collar 118b has a ramped distally-facing surface to allow the barbs 126e to pass proximally over the collar 118b during assembly, and a perpendicular proximally-facing surface to prevent the barbs 126e from passing back over the collar 118b. In this way, the hub subassembly 124 is retained on the coupling element 114.

A cap sleeve member 140 is fitted to the distal side of the hub subassembly 124. The cap sleeve member 140 has a distally-extending bore 142 that defines, in part, a cap chamber 144 or cannula chamber for receiving the distal end part 128a of the needle 128. The cap retaining part 126d of the hub body 126 engages with an interference fit in a proximal end of the bore 142, to form a seal between the cap sleeve member 140 and the hub body 126. In an alternative arrangement (not shown), an O-ring seal is provided between the cap sleeve member 140 and the cap retaining part 126d of the hub body 126.

A small-diameter bore 146 extends proximally from the distal end of the cap sleeve member 140 to connect with the distally-extending bore 142. The small-diameter bore 146 is plugged with a cylindrical closure 148 comprising an air-permeable sterile barrier material, such as are available under the registered trade marks Tyvek (DuPont, Del., USA) and Vyon (Porvair PLC., Norfolk, UK). The closure 148 allows air to flow into or out of the cap chamber 144 and the release member chamber 136 (through the flow path provided by the cannula 128) to equalise the pressure in the chambers 136, 144. This eliminates pressure gradients across the seals between the septum 112 and the coupling element 114, between the cap chamber 144 and the hub body 126, and between the hub body 126 and the cap sleeve member 140, reducing the risk of failure of these seals. The sterile barrier properties of the material of the closure 148 prevent microbial contamination of the cap chamber 144. In some cases (not illustrated), where equalisation of pressure is not required, the small-diameter bore 146 may be omitted so that the cap chamber 144 is closed and sealed by the distal end of the cap sleeve member 140.

The cap chamber 144 therefore provides an aseptically sealed compartment for the distal end part 128a of the needle 128. Provided the cap sleeve member 140 is engaged with the hub subassembly 124 in sterile conditions, the distal end part 128a of the needle 128 remains sterile until the device 101 is activated, as will be described further below.

Figure 3:
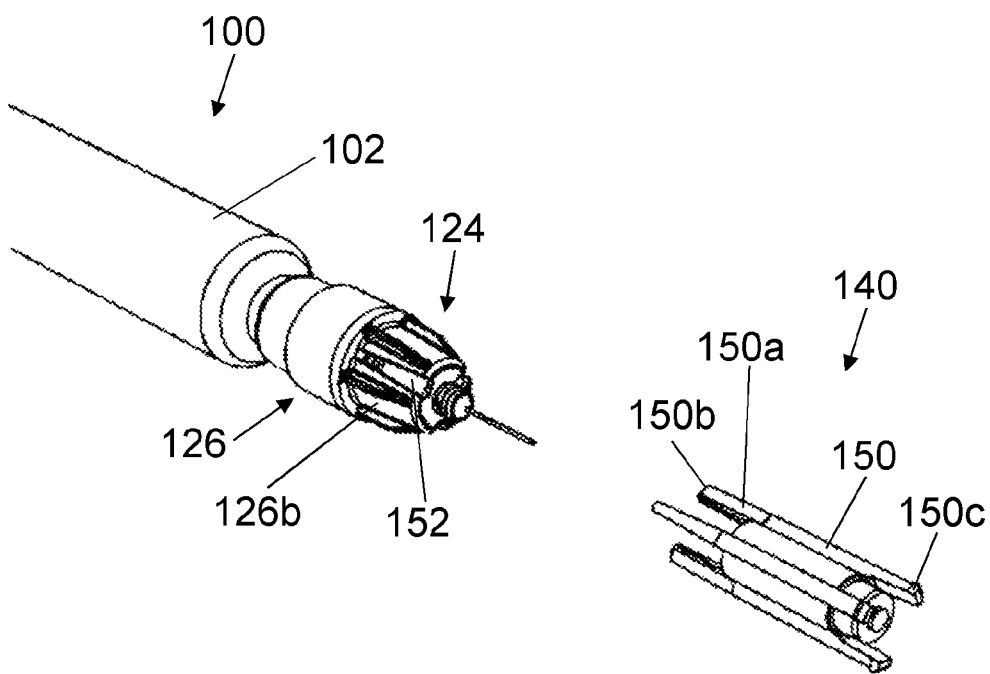
FIG. 3 is an exploded view showing parts of the device of FIG. 1.

FIG. 3 is a part-exploded view showing the cartridge assembly 100 engaged with the hub subassembly 124 and the cap sleeve member 140 separated from the hub subassembly 124, with the housing 12 and the outer cap 18 omitted. The cap sleeve member 140 is provided with a plurality of ribs 150. The ribs 150 extend parallel to the longitudinal axis of the cap sleeve member 140 and are disposed in an equi-angular arrangement around the outside of the cap sleeve member 140. In the illustrated example, three ribs 150 are provided, but fewer or more ribs 150 may be present.

Each rib 150 is extended proximally to form a blocking member or blocking finger 150a. Each blocking finger 150a is received in a corresponding aperture 152 in the distal part 126b of the hub body 126.

Referring back to FIG. 2, with the cap sleeve member 140 in place, the proximal end tip 150b of each blocking finger 150a is positioned to cooperate with the distal end face 118a of the throat 118 of the coupling element 114. Thus movement of the coupling element 114 in a distal direction with respect to the hub subassembly 124 or, equivalently, movement of the hub subassembly 124 in a proximal direction with respect to the coupling element 114 is blocked by abutment between the blocking finger 150a and the coupling element 114. The blocking fingers 150a therefore prevent the device 101 from moving out of a starting configuration in which the proximal end of the needle 128 is spaced apart from the septum 112. This arrangement advantageously prevents accidental activation of the device 101, for example in the event that the device 101 is dropped.

Each rib 150 is also extended distally to form a clip formation 150c. The clip formations 150c are separated from the distal end region of the cap sleeve member 140 by slots 150d, so that the clip formations 150c are flexible. The clip formations 150c are used to couple the cap sleeve member 140 to the outer cap 18 of the device 101.

The cartridge assembly 100, the hub subassembly 124 and the cap sleeve member 140 together define a packaging assembly that can be pre-assembled in the starting configuration in a sterile environment. By virtue of the chambers 136, 144 and the seals, all of the components of the packaging assembly that will come into contact with the medicament in use, as well as the medicament in the medicament chamber 104 and the distal end part 128a of the needle 128 (which passes into the injection site) subsequently remain sterile.

One convenient way of pre-assembling the packaging assembly comprises first attaching the septum 112, the crimp ring 122, the coupling element 114 and the cap sleeve member 140 to the hub subassembly 124 and sterilising these components to from a sterile cannula module. The cannula module can then be secured to the distal end of the cartridge 102 by crimping the crimp ring 122.

The packaging assembly as a whole can then be installed in the delivery device 101. Advantageously, the cap sleeve member 140, the hub body 126 and the coupling element 114 all have smaller diameters than the diameter of the cartridge 102 so that the packaging assembly can be inserted into a device housing from the proximal end of the housing.

The device 101 can therefore be assembled by inserting the packaging assembly (i.e. the cartridge assembly 100 and the attached hub subassembly 124) through the proximal end opening of the interior space 13 of the housing 12 and pushing the assembly distally until the clip formations 150c of the cap sleeve member 140 engage in corresponding slots 20 provided in the distal end face of the outer cap 18. In the illustrated embodiment, the outer cap 18 is engaged with the housing 12 before the packaging assembly is inserted, but equivalently the packaging assembly could be inserted to the housing 12 and held in place while the outer cap 18 is subsequently attached, or the outer cap 18 could be attached to the cap sleeve member 140 before insertion of the packaging assembly into the device 101 from its distal end. In each case, the presence of the blocking formations 150a prevent the hub assembly 124 and the cartridge assembly 100 moving towards one another during the insertion process, keeping the components in the starting configuration irrespective of any linear forces applied during handling.

The proximal end fitting 14 clips into the proximal end of the housing 12 to retain the cartridge assembly 100 in the housing 12. The proximal end fitting 14 also provides a guide bore 22 for an elongate plunger rod 24 of the plunger 16. A distal tip 26 of the plunger rod 24 is formed to engage with a corresponding recess 111 in the proximal side of the bung 110.

To prepare the device 101 for use, the outer cap 18 can be removed from the housing 12, as shown in FIG. 4. Because the cap sleeve member 140 is engaged with the outer cap 18, the cap sleeve member 140 is removed along with the outer cap 18, exposing the distal end part 128a of the needle 128 and withdrawing the blocking formations 150a from the apertures 152 in the hub body 126 in a linear movement.

To operate the device 101, the plunger 16 is pushed distally with respect to the housing 12. The force initially applied to the cartridge assembly 100, via the plunger rod 24 and the bung 110, causes the cartridge assembly 100 (i.e. the cartridge 102, the septum 112 and the coupling element 114) to move distally with respect to the hub subassembly 124, moving the throat 118 of the coupling element 114 into the distal part 126b of the hub body 126 as shown in FIG. 5.

The elastomeric sealing cap 130 disengages from the ridge 138, and the proximal end part 128b of the needle 128 pierces the septum 112 to connect the needle 128 to the medicament chamber 104. The device 101 is now in an activated state in which a flow path from the medicament chamber 104 to the distal end of the needle 128 has been established.

Delivery of the medicament through the needle 128 can then take place by further displacement of the plunger 16 in the distal direction.

Figure 6:
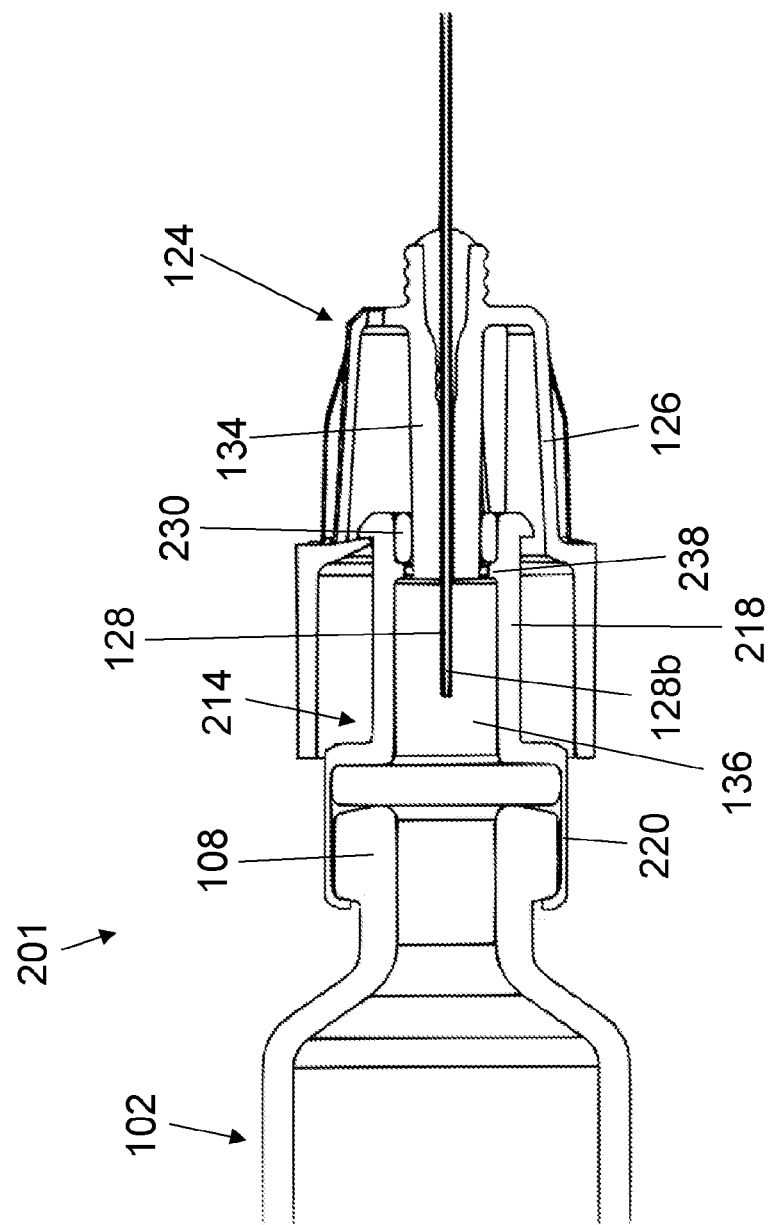
FIG. 6 is a cross-sectional view of part of another medicament delivery device according to the invention in a starting configuration.

FIG. 6 shows part of a device 201 according to another embodiment of the invention, which differs from the device 101 of FIGS. 1 to 5 in only two respects which will be described below. The structure and operation of the device 201 of FIG. 6 is otherwise identical to the previous embodiment. The cap sleeve member, the housing and the outer cap of the device 201 are not shown in FIG. 6.

In the FIG. 6 arrangement, the coupling element 214 is attached to the cartridge 102 by way of a crimp fitting that is formed integrally with the coupling element 214. In particular, the proximal end of the skirt 220 is deformed during assembly to clasp around the collar 108. In this embodiment, the coupling element 214 may be of a suitable ductile material such as aluminium.

Also, instead of an elastomeric sealing cap, in this embodiment a seal member comprising an elastomeric O-ring seal 230 is used to provide the aseptic seal between the boss 134 of the hub body 126 and the throat 218 of the coupling element 214. The O-ring seal 230 is kept in place by the ridge 238 on the interior wall of the throat 218. It will be appreciated that other arrangements are possible and that any suitable seal could be provided between the coupling element 214 and the hub subassembly to seal the proximal part 128b of the needle 128 in the chamber 136.

Figure 7A:
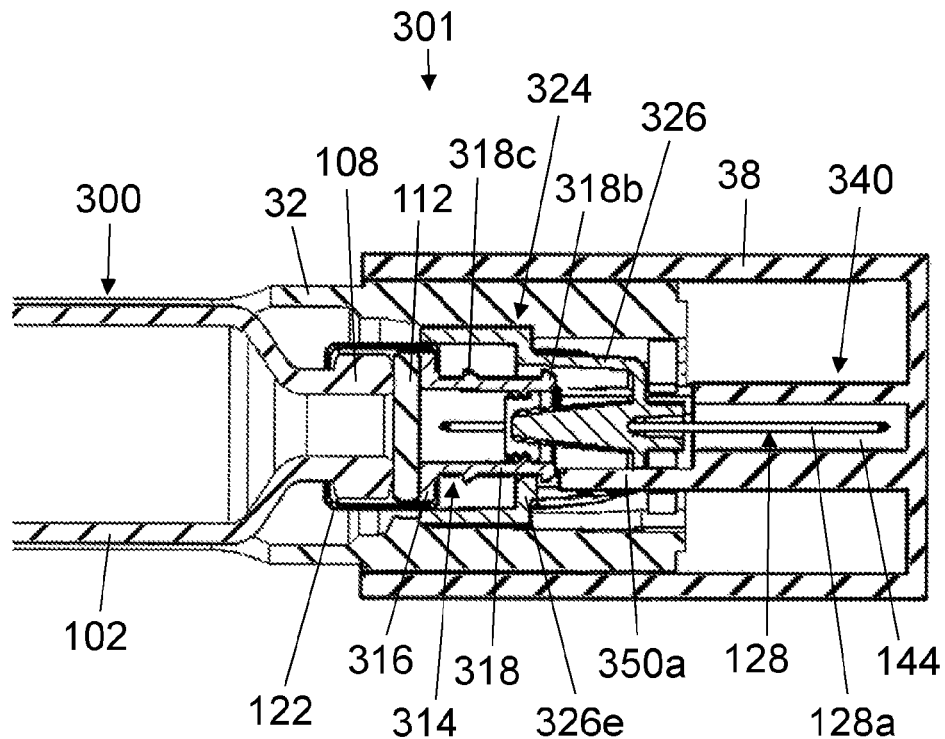
FIGS. 7(a) and 7(b) are cross-sectional views of part of a further medicament delivery device according to the invention in a starting configuration, before and after removal of a cap.
Figure 7B:
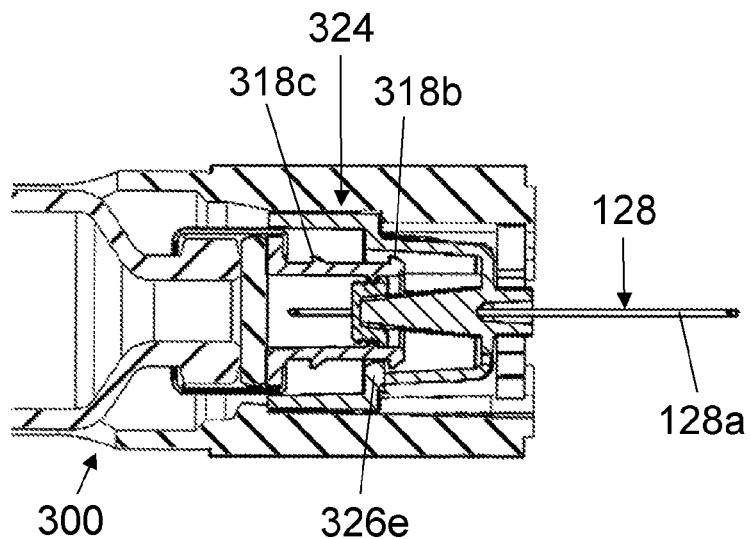

FIGS. 7(a) and 7(b) show part of another device 301 according to the invention, which is similar to the embodiments shown in FIGS. 1 to 6, and only the differences will be described in detail. FIG. 7(a) shows the device 301 with the outer cap 38 in place, and FIG. 7(b) shows the device 301 with the outer cap 38 removed.

In this case, the cap sleeve member 340 is formed integrally with the outer cap 38, as shown in FIG. 7(a). Accordingly, during assembly of the device 301, the outer cap 38 is engaged with the distal end of the housing 32, either before or after the cartridge assembly 300 and hub subassembly 324 are installed in the housing 32. In either case, engagement of the cap sleeve member 340 with the hub body 326 is performed under sterile conditions so that the distal end part 128a of the needle 128 remains sterile in the chamber 144. In this example the cannula chamber 144 is not vented, but a vent could be provided if desired.

In this embodiment, the coupling element 314 lacks a proximally-extending skirt. Instead, the coupling element 314 consists of the ring-shaped annular clamping portion 316 that bears against the septum 112 and the distally-extending tubular throat 318, and the crimp ring 122 extends over the neck 108 of the cartridge 102, the septum 112 and the clamping portion 316 to retain the coupling element 314 on the distal end of the cartridge 102.

The tubular throat 318 of the coupling element 314 comprises a second collar 318c disposed on the outside wall of the throat 318. The second collar 318c is at an intermediate position between the clamping portion 316 and the collar 318b at the distal end of the throat 318.

In use of the device 301, the outer cap 38 can be removed to uncover the distal end part 128a of the needle 128, as shown in FIG. 7(b). Removal of the outer cap 38 withdraws the blocking formations 350a from the hub body, so that the cartridge assembly 300 can move distally with respect to the hub subassembly 324 to switch the device into the activated configuration. The second collar 318c comes into engagement with the inwardly directed clips 326e to latch the cartridge assembly 300 and the hub subassembly 324 in position in the activated configuration.

Figure 8:
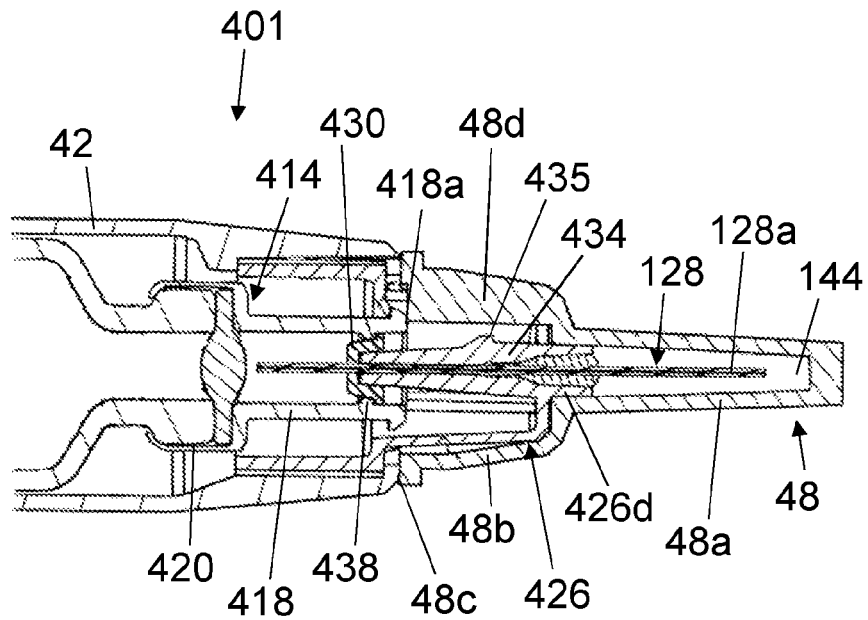
FIG. 8 is a cross-sectional view of part of a still further medicament delivery device according to the invention in a starting configuration.

FIG. 8 shows part of another device 401 according to the invention, which shares many features with the previously-described embodiments, and only the differences will be described in detail.

In this case, the skirt 420 of the coupling element 414 acts as the crimp ring, as described above with reference to FIG.

6, but the seal between the hub body 426 and the coupling element 414 comprises an elastomeric cap 430 as described above with reference to FIGS. 1 to 5.

In this embodiment, the proximally-extending boss 434 includes a projection 435 that has a ramped proximal side and a distal side that is perpendicular to the axis of the boss 434. When the device 401 switches from the starting configuration shown in FIG. 8 to the activated configuration, the projection 435 engages with the annular ridge 438 formed on the inner wall of the throat 418 of the coupling element 414.

In the FIG. 8 embodiment, a single-piece cap 48 is provided. The cap 48 does not include a vent, but a vent could be provided if desired. The cap 48 includes a tubular receiving portion 48a for receiving the distal end part 128a of the needle 128, with the receiving portion 48a engaging with the cap retaining part 426d of the hub body 426 to define the sealed chamber 144. A bell-shaped proximal portion 48b of the cap 48 extends around the hub body 126 and the proximal end face 48c of the cap 48 abuts a distal end face of the housing 42.

In this embodiment, the blocking formations comprise a plurality of radial ribs 48d, one of which can be seen in FIG. 8, that are accommodated within the proximal portion 48b of the cap 48. As in the previously-described embodiments, the proximal tips of the ribs 48d are positioned to cooperate with the distal end 418a of the coupling element 414 to prevent switching of the device 401 out of the starting configuration while the cap 48 is in place.

Figure 9:
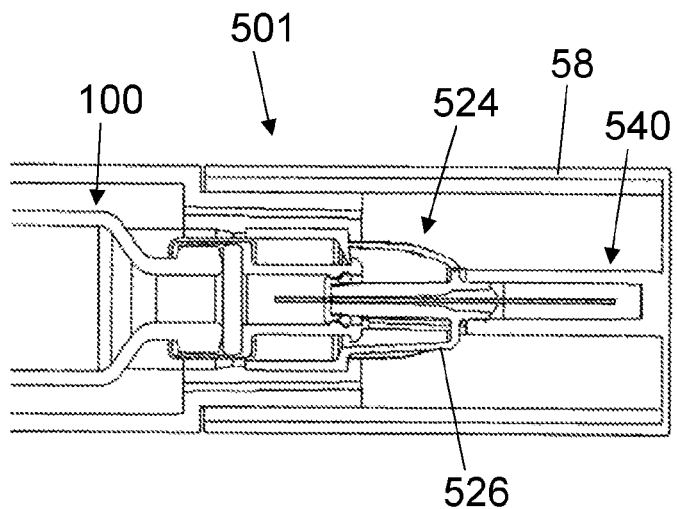
FIG. 9 is a cross-sectional view of part of another medicament delivery device in a starting configuration.

FIG. 9 shows part of another delivery device 501, which does not form part of the present invention.

The device 501 of FIG. 9 shares many features with the previously-described embodiments of the invention. In particular, the cap sleeve member 540 is formed integrally with the outer cap 58, as described above with reference to FIG. 7, and the cartridge assembly 100 and hub subassembly 524 are substantially as described with reference to FIGS. 1 to 5. However, in the device 501 of FIG. 9, the blocking members of the above-described embodiments are omitted, and the hub body 526 lacks the corresponding apertures.

Although FIGS. 1 to 9 illustrate devices in the form of a manual syringe, the arrangements described above can be used in a wide variety of different delivery devices. In particular, the same cartridge assembly and hub subassembly arrangements can be used in auto-injector devices in which one or more of the steps of needle insertion into an injection site, delivery of the medicament, retraction of the needle and shielding the needle may be driven by an energy source such as a spring.

Figure 10A:
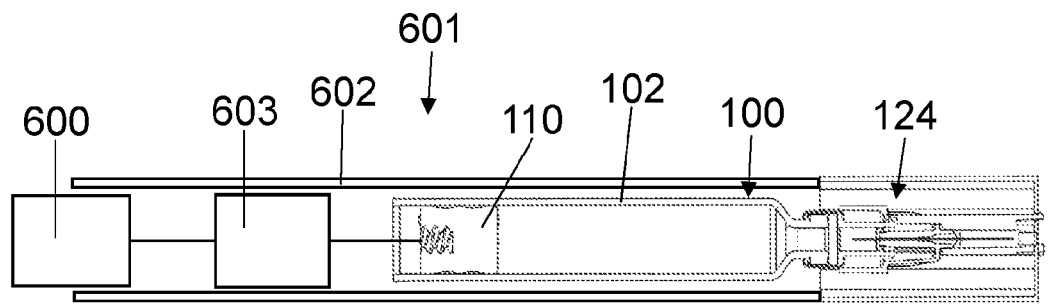
FIGS. 10(a), (b) and (c) show schematic cross-sectional views of further delivery devices according to the invention.

For example, FIG. 10(a) shows the cartridge assembly 100 and hub subassembly 124 described above with reference to FIGS. 1 to 5 installed in an auto-injector device 601 having a trigger mechanism 600 and a drive mechanism 603. In this case, the trigger mechanism 600 is operable by a user to cause the drive mechanism 603 to move the stopper or bung 110 in the distal direction with respect to the housing 602, for example using a drive spring. In this case, switching of the device 601 from the starting configuration to the activated configuration occurs during an initial phase of operation of the drive mechanism 603 in which distal movement of the bung 110 also causes distal movement of the cartridge assembly 100 with respect to the housing 602 and the hub subassembly 124. The drive mechanism 603 may also act as an insertion mechanism by driving the cartridge assembly 100 and the hub subassembly 124 together in the distal direction before delivery of the medicament. Suitable trigger mechanisms and drive mechanisms will be familiar to those skilled in the art.

Figure 10B:
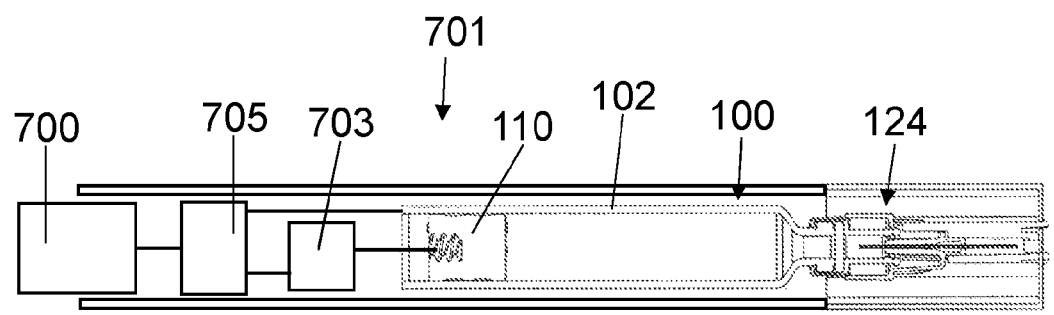

FIG. 10(b) shows the cartridge assembly 100 and hub subassembly 124 installed in another auto-injector device 701. In this case, the device 701 has a trigger mechanism 700 that operates an activating mechanism 705 which, in turn operates a drive mechanism 703. Operation of the trigger mechanism 700 by the user causes the activating mechanism 705 to displace the cartridge 102 in the distal direction with respect to the hub subassembly 124, switching the device 701 from the starting configuration to the activated configuration. Subsequently, the drive mechanism 703 displaces the bung 110 in the distal direction with respect to the cartridge 102 to deliver the medicament. Optionally, either the activating mechanism 705 or the drive mechanism 703 could be arranged also to cause insertion of the needle. Again, suitable mechanisms will be familiar to those skilled in the art.

Figure 10C:
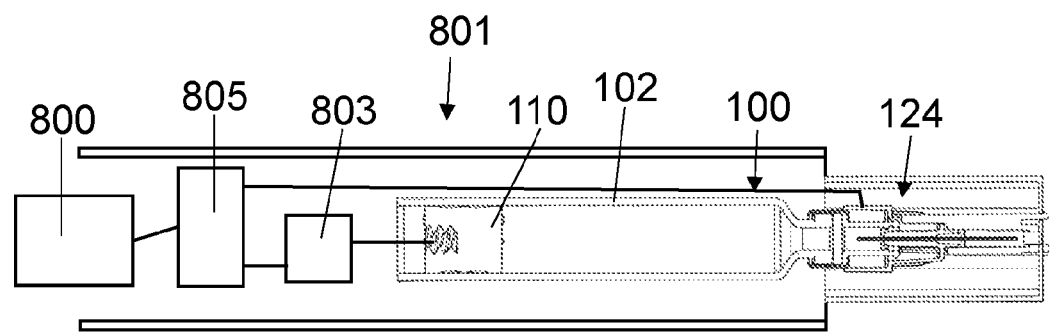

FIG. 10(c) shows the cartridge assembly 100 and hub subassembly 124 installed in another auto-injector device 801. This device 801 also has a trigger mechanism 800 that operates an activating mechanism 805 which, in turn operates a drive mechanism 803, but in this case operation of the trigger mechanism 800 by the user causes the activating mechanism 805 to displace the hub subassembly 124 proximal direction with respect to the cartridge 102, switching the device 801 from the starting configuration to the activated configuration. Subsequently, the drive mechanism 803 displaces the bung 110 in the distal direction with respect to the cartridge 102 to deliver the medicament. Optionally, either the activating mechanism 805 or the drive mechanism 803 could be arranged also to cause insertion of the needle. Again, suitable mechanisms will be familiar to those skilled in the art.

In the examples of FIG. 10, the trigger mechanism may be activated by a button disposed at a proximal end of the housing or by other means such as by a slider, a skin-contact sensor, telescoping housing parts, and so on, as will be familiar to those skilled in the art.

Further variations and modifications may be contemplated. For example, in the illustrated examples, the cannula is a double-ended needle, and the proximal end part of the needle acts as a piercing member for the septum. However, a single-ended needle could be provided for delivery of the medicament, with a separate piercing member being formed integrally with the hub body or as a separate component. It is also conceivable that, instead of a septum, the distal end of the cartridge could be sealed by a valve, rupturable membrane or other sealing device. In such cases the sealing element may be released by a suitable release member, which need not be a piercing member but could instead be arranged to open a valve, rupture a membrane and so on.

The cannula need not be a needle, but could instead be a flexible cannula or other suitable infusion or injection device. The cannula need not be mounted directly in the hub body but could instead be connected to the hub body by a flexible tube or the like.

In the illustrated examples, the coupling element is attached to the cartridge by a crimp fitting. The coupling element could instead be attached to the cartridge by any suitable means, including for example a clip arrangement and/or a retaining collar.

It will also be appreciated that the blocking formations need not extend through apertures in the hub body. The present invention extends to any arrangement in which a blocking formation of the cap cooperates with the cartridge assembly to maintain a clearance between the sealing element release member and the sealing element while the cap is in place.

Further modifications and variations not explicitly described above are also possible without departing from the scope of the invention as defined in the appended claims.

The invention claimed is:

1. A medicament delivery device comprising:
a cartridge assembly comprising a cartridge having a medicament chamber for containing a medicament, a seal for sealing a distal end of the medicament chamber, a coupling element attached to the cartridge;
a hub;
a seal release mounted in the hub;
a cannula for delivery of the medicament; and
a removable cap engageable with the hub;
wherein a release member chamber is defined in part by the coupling element and in part by the seal, the release member chamber being arranged for receiving the release such that at least a proximal end of the release is sealed in the release member chamber when the device is in a starting configuration in which the release is spaced from the seal;
wherein the cap comprises at least one blocking finger, the at least one blocking finger extending through a corresponding aperture in the hub to cooperate with the coupling element of the cartridge assembly when the cap is in place, a proximal end tip of the at least one blocking finger cooperating with a distal end face of the coupling element for limiting movement of the cartridge assembly in a distal direction toward the release, thereby to keep the device in the starting configuration in which the release is spaced from the seal when the cap is in place; and
wherein, after removal of the cap, the device is configured to undergo relative movement between the release and the cartridge assembly from the starting configuration to an activated configuration in which the release cooperates with the seal to connect the medicament chamber to the cannula.

2. A medicament delivery device according to claim 1, wherein the cap is disposed at a distal end of the device.

3. A medicament delivery device according to claim 1, wherein the at least one blocking finger comprises a proximally extending finger.

4. A medicament delivery device according to claim 1, wherein the at least one blocking finger comprises a radially inwardly projecting rib of the cap.

5. A medicament delivery device according to claim 1, wherein the release is fixed in position with respect to the cap when the cap is in place.

6. A medicament delivery device according to claim 1, wherein the hub is moveable with respect to a housing of the device and the cartridge assembly to switch the device from the starting configuration to the activated configuration.

7. A medicament delivery device according to claim 1, wherein the hub is fixed with respect to a housing of the device and the cartridge assembly is moveable with respect to the hub to switch the device from the starting configuration to the activated configuration.

8. A medicament delivery device according to claim 1, wherein the cannula is mounted in the hub.

9. A medicament delivery device according to claim 1, wherein the release member chamber is defined in part by the hub and wherein an aseptic seal is formed between the hub and the coupling element to seal the release member chamber at least when the assembly is in the starting configuration.

10. A medicament delivery device according to claim 9, wherein the hub comprises a proximally-projecting boss for the release and wherein the release member chamber is defined in part by a distally-projecting tubular member of the coupling element, the tubular member being arranged to receive the boss and the aseptic seal being formed between the tubular member and the boss at least when the assembly is in the starting configuration.

11. A medicament delivery device according to claim 9, comprising a seal member arranged to provide the aseptic seal between the hub and the coupling element.

12. A medicament delivery device according to claim 1, comprising a cannula chamber defined in part by the cap and arranged for receiving the cannula such that at least a distal end of the cannula is sealed in the cannula chamber when the cap is in place.

13. A medicament delivery device according to claim 12, wherein the cap comprises a cap sleeve member and an outer cap, the cannula chamber being defined in part by the cap sleeve member, the outer cap being engageable with a housing of the device and the cap sleeve member being engageable with the outer cap during assembly of the device.

14. A medicament delivery device according to claim 1, wherein the release comprises a tubular element arranged to pierce the seal upon switching of the assembly into the activated configuration.

15. A medicament delivery device according to claim 14, wherein the cannula comprises a distal part of a needle and the release comprises a proximal part of the needle.

* * * * *